US008314061B2

(12) United States Patent  
Morrow et al.

(10) Patent No.: US 8,314,061 B2
(45) Date of Patent: Nov. 20, 2012

(54) ADIPONECTIN FOR TREATMENT OF VARIOUS DISORDERS

(75) Inventors: Ardythe L. Morrow, Cincinnati, OH (US); Lisa J. Martin, West Chester, OH (US); David S. Newburg, Newtonville, MA (US)

(73) Assignees: Children's Hospital Medical Center, Cincinnati, OH (US); University of Massachusetts, Boston, MA (US)

( * ) Notice: Subject to any disclaimer, the term of this patent is extended or adjusted under 35 U.S.C. 154(b) by 441 days.

(21) Appl. No.: 12/160,335

(22) PCT Filed: Jan. 9, 2007

(86) PCT No.: PCT/US2007/060270
§ 371 (c)(1),
(2), (4) Date: Apr. 15, 2009

(87) PCT Pub. No.: WO2007/087468
PCT Pub. Date: Aug. 2, 2007

(65) Prior Publication Data
US 2009/0197806 A1    Aug. 6, 2009

(51) Int. Cl.
*C07K 14/00* (2006.01)
(52) U.S. Cl. ............................................. 514/2; 530/300
(58) Field of Classification Search .................. None
See application file for complete search history.

(56) References Cited

U.S. PATENT DOCUMENTS

| 7,363,076 | B2 | 4/2008 | Yun et al. ...................... 607/3 |
| 7,365,170 | B2 | 4/2008 | Cooper et al. ............... 530/399 |
| 2006/0211752 | A1* | 9/2006 | Kohn et al. .................. 514/389 |
| 2008/0095821 | A1* | 4/2008 | Fogelman et al. ........... 424/423 |

FOREIGN PATENT DOCUMENTS

| WO | 02/072149 A1 | 9/2002 |
| WO | WO 03/055916 A2 | 7/2003 |
| WO | WO 03/062275 A1 | 7/2003 |

OTHER PUBLICATIONS

Wikipedia, searched Adiponectin (PDF downloaded on Mar. 25, 2012).*
Mitchell et al., "Adipokines: Implications for Female Fertility and Obesity" Reproduction 130:583-597, 2005.
Weyer et al., "Hypoadiponectinentia in Obesity and Type 2 Diabetes . . ." J. of Clin. Endoc. & Metabol. 86(5):1930-1935, 2001.
Masaki, T., et al., "Peripheral, but not Central, Administration of Adiponectin Reduces Visceral Adiposity and Upregulates the Expression of Upcoupling Protein in Agouti yellow ($A^y/a$) Obese Mice", *Diabetes*, 52:2266-2273 (Sep. 2003).
Wang, Y. et al. "Hydroxylation and Glycosylation of the Four Conserved Lysine Residues in the Collagenous Domain of Adiponectin", *J. Biol. Chem.*, 277(22):19521-19529 (May 31, 2002).
Martin et al., Pediatric Res, vol. 55, No. 4, Suppl. S, Part 2, p. 36A (205) (2004).

* cited by examiner

*Primary Examiner* — Anand Desai
(74) *Attorney, Agent, or Firm* — Wolf, Greenfield & Sacks, P.C.

(57) ABSTRACT

Methods for treating various disorders by orally administering adiponectin or a biologically active fragment thereof are described.

11 Claims, 8 Drawing Sheets

Figure 1: Milk Adiponectin and Leptin Concentrations

Figure 3: Milk Adiponectin Concentration by Ethnicity

ADIPONECTIN FOR TREATMENT OF VARIOUS DISORDERS

RELATED APPLICATIONS

This application is a U.S. National Stage Filing under 35 U.S.C. 371 of International Application No. PCT/US2007/060270, filed on Jan. 9, 2007, which claims the benefit of U.S. Provisional Application No. 60/757,362 filed on Jan. 9, 2006.

BACKGROUND

Breast fed children tend to be healthier, with lower incidence of allergy and infectious disease, and tend to be leaner than formula fed children [1]. Although the reasons for these protective effects are not completely understood, milk proteins clearly play a role. In addition, previous studies have demonstrated that human milk proteins influence gastrointestinal, neural, and immunologic development in the nursing infant [2-6].

Adiponectin (also called ACRP30, adipoQ or GBP28), a protein produced primarily in adipose tissue by adipocytes [7-10], influences several physiologic processes that may impact human development. High concentrations of circulating adiponectin have positive health effects through the reduction of pro-inflammatory cytokines [11, 12], improvement of insulin sensitivity [13], and increase of fatty acid metabolism [14].

Human milk composition exhibits variation within and between lactating women. Intra-individual variation is likely due in part to changes in milk protein concentrations throughout lactation [15-17]. Inter-individual variability in milk protein concentrations has been attributed to genetic variation [18, 19] and maternal adiposity [20] among other factors.

In humans, adiponectin levels are inversely correlated with insulin resistance independent of adiposity [21-23], with the lowest levels of adiponectin in individuals with type 2 diabetes [24-26]. Furthermore, low adiponectin precedes the development of insulin resistance, suggesting a direct effect of adiponectin on insulin sensitivity [27-33]., Mouse studies have confirmed that adiponectin improves glucose utilization [34]. High adiponectin has also been associated with an anti-atherogenic lipid profile. Adiponectin is consistently inversely correlated with plasma triglycerides (TG) and positively correlated with plasma HDL cholesterol levels [35]. Adiponectin directly influences lipid metabolism and oxidation. Additionally, adiponectin has strong anti-inflammatory properties. Adiponectin decreases TNF-α [11] and IL-6 [11, 12] production, and increases expression of anti-inflammatory cytokines in macrophages [36]. Adiponectin also works downstream of TNF-α to suppress its ability to activate the NF-κB pathway [37]. Adiponectin inhibits the formation of granulocyte-macrophage colonies in vitro, and inhibits the phagocytic activity of mature macrophages [38].

Adiponectin exists in several oligomeric forms in vivo, the most common of which are trimers, hexamers or low molecular weight (LMW) forms, and double hexamers and higher-order structures that together are considered high molecular weight (HMW) forms.

Specific oligomers of adiponectin are associated with important metabolic outcomes in humans. The HMW form of circulating adiponectin is selectively increased in response to weight loss [39, 40] and is selectively decreased in response to infusion of insulin [41]. This is of particular interest because the HMW form of adiponectin is associated with changes in physiologic processes known to be strongly influenced by obesity: The proportion of adiponectin bound together as HMW complexes is better associated with glucose tolerance than total adiponectin levels [42]. Improvements in hepatic insulin sensitivity after treatment with anti-diabetic drugs are also more associated with the proportion of adiponectin present as HMW complexes than total adiponectin concentration [43]. HMW complexes constitute a lower percentage of total adiponectin in adults with coronary artery disease, compared with normal controls, and only the HMW form protects vascular endothelial cells from apoptosis [39]. The HMW complex is also more positively correlated with the anti-atherogenic high-density lipoprotein (HDL) cholesterol than total adiponectin, while the trimeric form is inversely associated with HDL [40].

Adiponectin oligomeric structures appear to be assembled within the cell and secreted, with little spontaneous interchange between the complexes at physiologic conditions [41, 44]. Indeed, Wang et al. [45] suggested that hydroxylation and glycosylation of specific amino acids the adiponectin gene account for the different oligomeric forms.

SUMMARY

Described herein are methods and compositions for treating or reducing the risk of obesity and certain metabolic disorders in infants and children. The methods entail administering a composition comprising adiponectin, e.g., a glycosylated form of adiponectin. In certain embodiments, the adiponectin has the amino acid sequence of adiponectin found in human milk. In some embodiments, the adiponectin has the glycosylation pattern of adiponectin found in human milk.

Human adiponectin precursor protein (GenBank® Accession No. NP_004788.1 GI:4757760) has the sequence below (the first 14 amino acid or the first 17 amino acids being the leader sequence and the remainder of the sequence being that of the mature protein).

```
                                        (SEQ ID NO: 1)
MLLLGAVLLLLALPGHDQETTTQGPGVLLPLPKGACTGWMAGIPGHPGHN

GAPGRDGRDGTPGEKGEKGDPGLIGPKGDIGETGVPGAEGPRGFPGIQGR

KGEPGEGAYVYRSAFSVGLETYVTIPNMPIRFTKIFYNQQNHYDGSTGKF

HCNIPGLYYFAYHITVYMKDVKVSLFKKDKAMLFTYDQYQENNVDQASGS

VLLHLEVGDQVWLQVYGEGERNGLYADNDNDSTFTGFLLYHDTN
```

Mature adiponectin has the following amino acid sequence: GHDQETTTQGPGVLLPLPKGACTGWMAG-IPGHPGHNGAPGRDGRDGTPGEK GEKGDPGLIGP-KGDIGETGVPGAEGPRGF-PGIQGRKGEPGEGAYVYRSAFSVG LETYVTIPNMPIRFTKIFYNQQNHYDG-STGKFHCNIPGLYYFAYHITVYMKDV KVSLFKKD-KAMLFTYDQYQENNVDQASGSV-LLHLEVGDQVWLQVYGEGER NGLYADNDNDSTFTGFLLYHDTN (SEQ ID NO:2) or the following amino acid sequence:

```
                                        (SEQ ID NO: 3)
QETTTQGPGVLLPLPKGACTGWMAGIPGHPGHNGAPGRDGRDGTPGEKGE

KGDPGLIGPKGDIGETGVPGAEGPRGFPGIQGRKGEPGEGAYVYRSAFSV

GLETYVTIPNMPIRFTKIFYNQQNHYDGSTGKFHCNIPGLYYFAYHITVY
```

-continued

MKDVKVSLFKKDKAMLFTYDQYQENNVDQASGSVLLHLEVGDQVWLQVYG

EGERNGLYADNDNDSTFTGFLLYHDTN

In some cases it can be desirable to administer a polypeptide fragment of SEQ ID NO:1 that includes some or all of the so-called globular head of adiponectin. For example, one can orally administer a composition comprising (consisting of or consisting essentially of) amino acids: 84-244, 85-244, 86-244, 87-244, 88-244, 89-244, 90-244, 91-244, 92-244, 93-244, 94-244, 95-244, 96-244, 97-244, 98-244, 99-244, 100-244, 101-244, 102-244, 103-244, 104-244, 105244, 106-244, 107-244, 108-244, 109-244, 110-244 or 111-244 of SEQ ID NO:1 (full-length human adiponectin). In other cases one can orally administer a composition containing a polypeptide fragment of SEQ ID NO:1 comprising, consisting of or consisting essentially a polypeptide fragment of amino acids: 84-244, 85-244, 86-244, 87-244, 88-244, 89-244, 90-244, 91-244, 92-244, 93-244, 94-244, 95-244, 96-244, 97-244, 98-244, 99-244, 100-244, 101-244, 102-244, 103-244 104-244, 105-244, 106-244, 107-244, 108-244, 109-244, 110-244 or 111-244 of SEQ ID NO:1 (full-length human adiponectin).

In some cases one can orally administer a composition comprising a trimer (complex of three polypeptide chains), hexamer (complex of 6 polypeptide chains), 12mer (complex of 12 polypeptide chains) or 18mer (complex of 18 polypeptide chains).

Several lysine residues in the protein have the potential to be glycosylated (e.g., lysine 65, 68, 77 and 101 referring to the numbering of the immature protein) and several proline residues have the potential to be hydroxylated.

In some cases, a useful composition containing adiponectin is relatively enriched in adiponectin relative to some or all of the components present in human milk. For example, the adiponectin can be 10%, 20%, 50%, 70%, 90% or more enriched relative to one or more of the proteins and fats (or all of the components) in human milk.

Described herein is a method for treating or reducing the risk of obesity in a patient comprising orally administering a composition comprising purified adiponectin or a fragment thereof, a method of treating or reducing the risk of metabolic syndrome in a patient comprising orally administering a composition comprising purified adiponectin or a fragment thereof; a method of treating or reducing the risk of a disorder selected from inflammatory bowel disease, hyperglycemia, insulin resistance, metabolic syndromes associated with insulin resistance, Type 2 diabetes mellitus, metabolic syndromes including hypertension, artherosclerosis, coronary heart disease or ischemic heart disease in a patient comprising orally administering a composition comprising purified adiponectin or a fragment thereof, and a method of treating or reducing the risk of necrotizing enterocolitis in an infant comprising orally administering a composition comprising purified adiponectin or a fragment thereof.

In some cases, the adiponectin or fragment thereof can be orally administered to: reduce body mass, reduce the rate of increase in body mass, treat glucose intolerance, treat insulin resistance, treat type II diabetes, treat hyperlipidemia, treat hyperuricemia, control blood glucose, treat patients with elevated fasting glucose that are not suffering from diabetes.

In some cases, the adiponectin or fragment thereof is administered to a patient that is also being administered insulin or an insulin sensitizing agent (e.g., metformin).

In various embodiments: the patient is less than 18 years old; the patient is less than 15 years old; the patient is less than 10 years old; the patient is less than 1 year old; and the patient is an infant that was born prematurely.

In some instances the adiponectin or fragment thereof is glycosylated. In other instances is it hydroxylated and glycosylated. In various embodiments: at least one amino acid of the adiponectin or fragment thereof is substituted with a glucosylgalactosyl residue; the adiponectin comprises the amino acid sequence of SEQ ID NO:1, 2 or 3 and is glycosylated at one or more of lysine residues 65, 68, 77 and 101. In other embodiments, the adiponectin comprises the amino acid sequence of SEQ ID NO:2. In some cases a polypeptide comprising SEQ ID NO:2 is glycosylated at one or more of lysines 51, 54 and 87.

In some cases the adiponectin is in the form found in human milk, e.g., the glycosylation of the purified adiponectin is that same as that found in human milk.

In some circumstances the purified adiponectin bears at least one moiety selected from a glucosylgalactosyl moiety, a glucosylglucosyl moiety, a galactosylglucosyl moiety, or a galactosylgalactosyl moiety.

A composition comprising purified adiponectin or a biologically active fragment thereof can further comprise an oligosaccharide found in human milk. In various cases, the composition comprises: at least one α1,2-linked fucosylated oligosaccharide or at least one oligosaccharide selected from: lacto-N-fucopentaose I [LNF-I], 2-fucosyllactose [2'-FL], lacto-N-difucohexaose I [LDFH-I], lactodifucotetraose [LDFT]), lacto-N-fuco-pentaose II [LNF-II], 3-fucosyllactose [3-FL], lacto-N-fucopentaose III [LNF-III], lacto-N-tetraose [LNT], and lacto-N-neotetraose [LNneoT].

In some cases the purified adiponectin or fragment there of is modified to include at one group groups selected from: Lacto-N-fucopentaose I; Lacto-N-fucopentaose II; 3'-Fucosyllactose; Lacto-N-fucopentaose II; Lacto-N-difucohexaose I; actodifucotetraose; LactoN-tetraose; LactoN-neotetraose; 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyllacto-N-neohexaose I; Monosialyllacto-N-neohexaose II; Disialyllacto-N-neohexaose; Disialyllacto-N-tetraose; Disialyllacto-N-hexaose II; Sialyllacto-N-tetraose a; Disialyllacto-N-hexaose I; Sialyllacto-N-tetraose b; 3'-Sialyl-3-fucosyllactose; Disialomonofucosyllacto-N-neohexaose; Monofucosylmonosialyllacto-N-octaose (sialyl Lea); Sialyllacto-N-fucohexaose II; Disialyllacto-N-fucopentaose II; and Monofucosyldisialyllacto-N-tetraose.

In some cases the n the purified adiponectin or biologically active fragment thereof bears at least one moiety selected from a glucosylgalactosyl moiety, a glucosylglucosyl moiety, a galactosylglucosyl moiety, or a galactosylgalactosyl moiety.

In various cases the adiponectin or biologically active fragment thereof is orally administered so as to achieve a plasma concentration of between 100 µg/ml and 100 µg/ml; between 10 µg/ml and 75 µg/ml; between 20 µg/ml and 60 µg/ml; or between 1 µg/ml and 100 µg/ml.

In various aspects of the methods described herein the adiponectin is administered so as to achieve a plasma concentration of adiponectin between 10 µg/ml and 100 µg/ml; the adiponectin is administered so as to achieve a plasma concentration of adiponectin between 10 µg/ml and 75 µg/ml; the adiponectin is administered so as to achieve a plasma concentration of adiponectin between 20 µg/ml and 60 µg/ml; and the adiponectin is administered so as to achieve a plasma concentration of adiponectin between 1 µg/ml and 100 µg/ml.

Also describe are a nutritional supplement comprising purified adiponectin and an infant formula comprising purified adiponectin.

A "purified protein" (e.g., purified adiponectin), as used herein, refers to a protein that has been separated from other proteins, lipids, and nucleic acids with which it is naturally associated. The protein can constitute at least 10, 20, 50 70, 80 or 95% by dry weight of the purified preparation.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
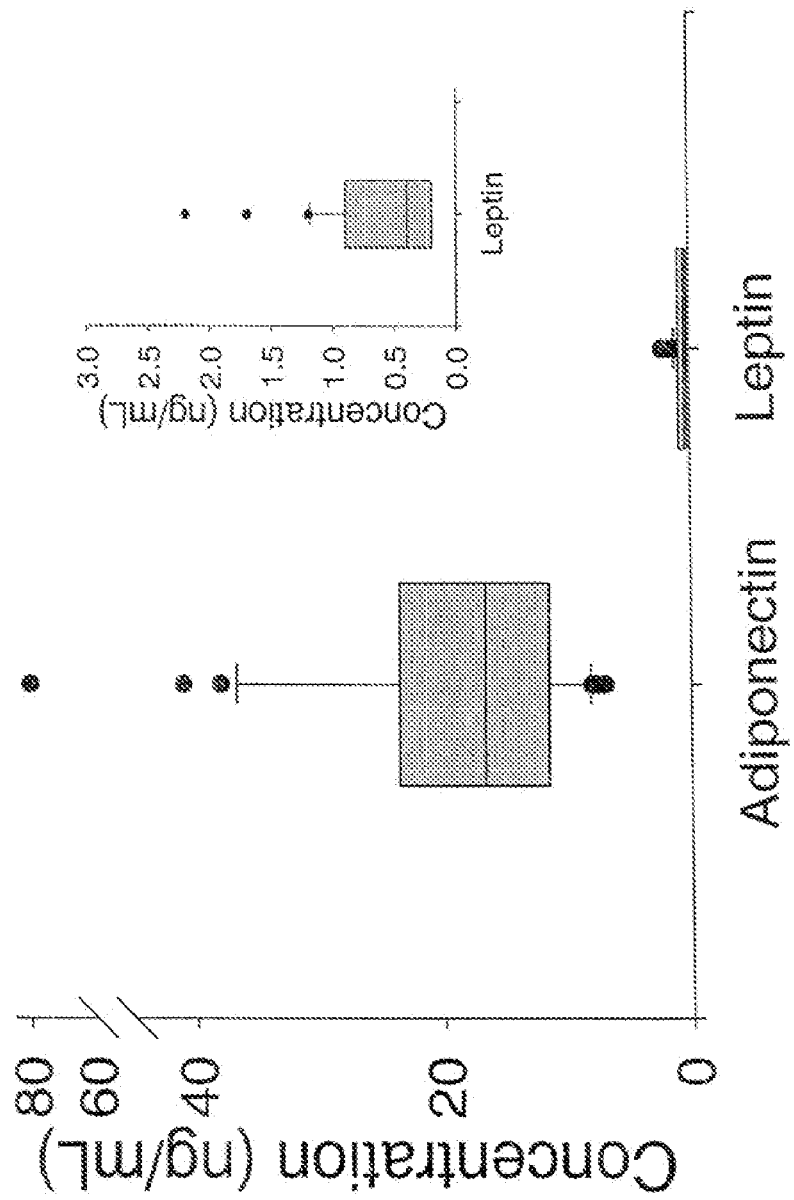
FIG. 1 is graph depicting a comparison of milk adiponectin and leptin concentrations and (inset) detail of milk leptin distribution in 30 cross-sectional milk samples from the RHMB-Ad hoc cohort. Interquartile range defined by box; median represented by horizontal line. Whiskers represent 95th and 5th percentiles of distribution. Difference between medians: $p<0.0001$ by Wilcoxon Signed Rank test.

Described below are studies demonstrating that adiponectin is present in human milk and its concentrations are associated with duration of lactation, ethnicity, and maternal adiposity. The presence of adiponectin in human milk and the fact that breast fed children are leaner than those fed formula suggests that adiponectin would be useful for treating infants to treat or reduce the risk of obesity and to treat or reduce the risk of other metabolic disorders.

EXAMPLE 1

Milk Samples

We analyzed human milk samples from two distinct populations of women: 1) donors to the Cincinnati Children's Research Human Milk Bank (RHMB) in Cincinnati, Ohio, and 2) participants from an NICHD-funded grant entitled "The Role of Human Milk in Infant Nutrition and Health" (P01 HD 13021; PI: Morrow) in Mexico City. These two populations were chosen because of the availability of milk samples using uniform collection procedures. The Institutional Review Board (IRB) at Cincinnati Children's Hospital Medical Center approved the protocols and consent forms for both of these studies, and the IRB at the National Institute of Medical Sciences and Nutrition in Mexico City also approved the protocol for the Mexican population.

The Cincinnati Children's Research Human Milk Bank (RHMB) is a repository in which any lactating women may voluntarily donate breast milk as either a one-time donation (RHMB-Ad hoc cohort) or regularly throughout the course of lactation (Cincinnati Breastfeeding Cohort, or RHMB-longitudinal) [46].

For the RHMB-Ad hoc cohort, the following information is collected at the time of donation: gestational age of the infant at delivery, day of lactation when milk was expressed, volume donated, and whether the milk was brought for donation to the bank fresh or frozen. However, as the mothers provide the expressed milk, this is a non-standardized collection. From the RHMB-Ad hoc cohort, 30 cross-sectional milk samples from donor mothers were randomly selected for this analysis.

For women who wish to take part in the longitudinal donation protocol (RHMB-longitudinal), a more extensive process is involved. To be a longitudinal donor, mothers must provide consent within one week after delivery, and all infants must be full-term (at least 37 weeks gestation), singleton infants without any congenital or medical complications. Mothers must commit to breastfeed, at least partially, for at least six months, speak English, and live within a 25-mile radius from the medical center. Women of all races and ethnic groups are eligible. Milk collection in the RHMB-longitudinal follows a standardized procedure (see Milk collection, below). To be selected for this analysis from the RHMB-longitudinal cohort, mothers had to donate at least seven samples by 7 months of lactation. A total of 199 milk samples from 22 mothers were included in this study.

At the time of the first visit, the research nurse conducts an extensive questionnaire-based interview. Data collected during this interview include demographics, reproductive history, previous breastfeeding experience, general health status of the mother and infant since birth, and medication and environmental exposure. During subsequent visits, an abbreviated questionnaire is administered to obtain updates on medications, health status, etc. Maternal anthropomorphic measurements are taken during each home visit with portable scales that are calibrated regularly.

The Mexican Human Milk study cohort is a collaborative effort between Cincinnati Children's Hospital Medical Center and the National Institute of Medical Sciences and Nutrition in Mexico City. Mothers were included in the study if they had a healthy, full-term infant born without congenital malformations, and if the mother intended to breastfeed.

Mothers received three visits from a peer counselor to support exclusive breastfeeding. Mothers provided milk samples weekly for the first month and then monthly for the duration of lactation. No data on maternal height or weight or infant gestational age at birth was collected. From the Mexican cohort, 37 mothers were randomly selected from subjects who had donated milk samples at approximately one-month lactation. Characteristics of all selected participants in the three cohorts are described in Table 1.

TABLE 1

Description of Study Cohorts

| | Research Human Milk Bank (RHMB) | | |
|---|---|---|---|
| | Ad hoc | Longitudinal | Mexico |
| N mothers | 30 | 22 | 37 |
| N samples | 30 | 199 | 37 |
| Data Structure | Cross-sectional | Longitudinal | Cross-sectional |
| Days of lactation sampled (range) | 1-401 | 4-242 | 31-40 |
| Race/Ethnicity | | | |
| Non-Hispanic White | 30 | 19 | 0 |
| Hispanic/Mexican | 0 | 0 | 37 |
| Other | 0 | 3 | 0 |
| Gestational age, weeks (range) | 34-42 | 38-42 | N/A* |
| Maternal post-pregnancy BMI, kg/m² median (range) | N/A | 24.5 (19.5, 34.2) | N/A |

*All infants were full-term

Milk Collection

For the RHMB-Ad hoc cohort, milk collection involved the mother bringing her milk sample to the RHMB at Cincinnati Children's Hospital Medical Center. For the RHMB-longitudinal and Mexico breastfeeding cohorts, milk collection occurred during home visits by the study nurse, for the duration of lactation. Milk collection involved draining an entire breast using a standard electric pump. A single study nurse for each cohort collected milk between 10:00 am and 1:00 pm. Collected milk was stored on ice for transportation to the local institution, where it was aliquotted and frozen at −80° C.

Maternal Anthropometrics

In the RHMB-longitudinal cohort only, a single trained research nurse measured maternal anthropometrics (B.S.D.). Maternal weight was measured at each monthly visit using an E-Z Carry Portable Digital Scale (Hopkins Medical Products, Baltimore, Md.). Women were measured in street clothing without shoes. Height was measured at the initial visit with the subject in the standing position wearing socks, heels together, toes apart at a 45 degree angle and head in the Frankfort horizontal plane. The height was marked on the wall and the vertical distance to the floor was measured. Body mass index (BMI) was calculated as weight in kg divided by the square of height in meters (kg/m2).

Assay of Adiponectin and Leptin

Because lipids interfere with radioimmunoassays (RIA), skimmed milk was used, and the same individual (W.B.) assayed all samples from the three cohorts. Milk samples were thawed and vortexed. Skim milk (aqueous phase) was prepared by centrifugation (1,500 μg, 20 min, 4° C.) after which the fat layer was removed. Immunoreactive adiponectin was measured in duplicate using a commercial RIA kit (Linco Research, St. Charles, Mo.) using a 100 μL of a 1:3 dilution of skim milk (33.3 μL equivalent). The inter- and intra-assay coefficients of variation were 8.5 and 3.9% respectively. In the RHMB-Ad hoc samples, leptin was also assayed in duplicate in skim milk using a commercial RIA kit (Linco Research, St. Charles, Mo.) following the protocol of Houseknecht and colleagues [47]. The inter- and intra-assay CVs were 4.5 and 5.0%, respectively, with a limit of detection of 0.3 ng/mL.

The assay methods for adiponectin were validated using standards, and skim milk samples were spiked with the 5, 20, and 100 ng/mL human adiponectin standard to determine the recovery of added mass.

Statistical Analyses

Statistical analyses were conducted using SAS version 9.1.3. Descriptive statistics are reported as medians and ranges, due to non-normality of the data. To improve normality of milk adiponectin for use in statistical models, the data were natural log(ln) transformed. Eight milk leptin concentrations were below the limit of detection (0.3 ng/mL), these values were set at 0.2 ng/mL. Analyses were also conducted with the values below the detection limit set at 0; however, the results did not change substantially and thus are not reported.

To examine the effect of lactation on ln(milk adiponectin) concentrations, we used RHMB Ad hoc and longitudinal data. In cross-sectional analyses, linear regression models were constructed using ln(milk adiponectin) as the dependent variable. In the longitudinal analyses, mixed models with repeated measures were constructed where intercepts for each donor is treated as random. The best correlation structure (in this case equal correlation among ln(milk adiponectin) obtained across different time points) is selected using the Bayesian Information Criterion (BIC) derived based on the data. The dependent variable was ln(milk adiponectin) and the independent variable was day of lactation.

To determine the effect of ethnicity on milk adiponectin concentrations, median milk adiponectin at approximately one-month lactation from non-Hispanic whites in the RHMB-longitudinal cohort (range: 26 to 42 days) and Hispanics in the Mexican cohort (range: 31 to 40 days) were compared using a Wilcoxon Rank Sum test.

To determine the effect of maternal adiposity on milk adiponectin concentrations, maternal BMI from the RHMB-longitudinal cohort was examined cross-sectionally and longitudinally. In cross-sectional analyses, ln(milk adiponectin) was regressed against maternal BMI at each time point. In longitudinal analyses, repeated measures of ln(milk adiponectin) was modeled as influenced by repeated measures of maternal BMI mixed model procedures.

Validation of Adiponectin Assay for Human Milk.

Adiponectin concentrations of serial dilutions (10-40 μL) of skim milk were parallel to the standard curve. Skim milk samples were spiked with the 5, 20, and 100 ng/mL human adiponectin standard, and recovery of added mass averaged 109%.

Adiponectin and Leptin in Human Milk

Immunoreactive adiponectin was detected in skim milk in all samples (Table 2). Milk adiponectin concentration was not associated with gestational age ($p \geq 0.18$).

TABLE 2

Human Milk Adiponectin and Leptin Concentrations

| | Research Human Milk Bank (RHMB) | | |
|---|---|---|---|
| | Ad hoc | Longitudinal | Mexico |
| Milk adiponectin | 16.6 (6.9, 80.4) | 17.7 (4.2, 87.9) | 11.7 (6.2, 39.8) |

TABLE 2-continued

Human Milk Adiponectin and Leptin Concentrations

| | Research Human Milk Bank (RHMB) | | |
|---|---|---|---|
| | Ad hoc | Longitudinal | Mexico |
| concentration, ng/mL median (range) | | | |
| Milk leptin concentration, ng/mL median (range) | 0.4 (ND [0.2], 2.2) | N/A | N/A |

In the RHMB-Ad hoc samples, both leptin and adiponectin concentrations were assayed in milk (FIG. 1). Median adiponectin concentrations were over 40 times greater than leptin concentrations (16.6 versus 0.4 ng/mL, respectively, p<0.0001 by Wilcoxon Rank Sum test). Concentrations of milk adiponectin and milk leptin were positively correlated with each other (Spearman r=0.37, p=0.046).

The concentration of adiponectin in milk is much lower than in serum. In neonates, serum adiponectin concentrations have been reported to range from 20-60 ug/mL [48, 49] while we found milk adiponectin concentrations to range from 4.2 to 87.9 ng/mL. However, milk adiponectin concentrations are consistent with concentrations of expressed adiponectin mRNA from mesenteric adipose tissue [50], perhaps suggesting local effects.

Leptin is the only other adipokine that has been measured in human milk [47, 51-53]. In the RHMB-Ad hoc samples in this study, milk leptin concentrations were forty-fold lower than adiponectin. The leptin concentrations in milk measured in this study were slightly lower than reported for leptin in other studies [20, 47, 51]. The lower concentrations may be due to the extended lactation period examined in this study.

Adiponectin Declines through Lactation

Figure 2:
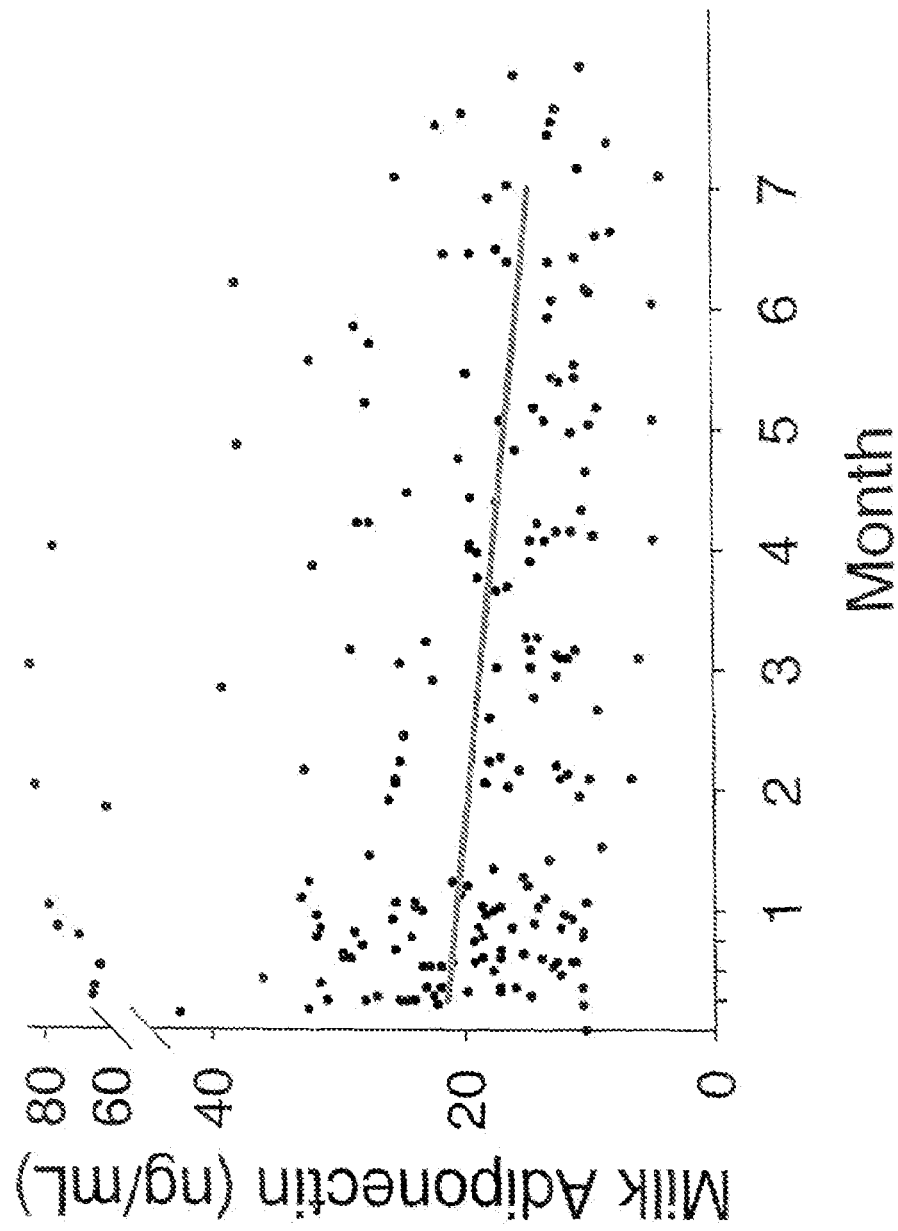
FIG. 2 is a graph depicting the relationship between milk adiponectin and duration of lactation. Solid line is the predicted regression line determined from the repeated measures analysis of month of lactation and ln(milk adiponectin): $\beta \pm SE$: $-0.059 \pm 0.007$. A total of three data points from two individuals are not presented, with milk adiponectin concentrations between 45 and 60 ng/mL.
Figure 3:
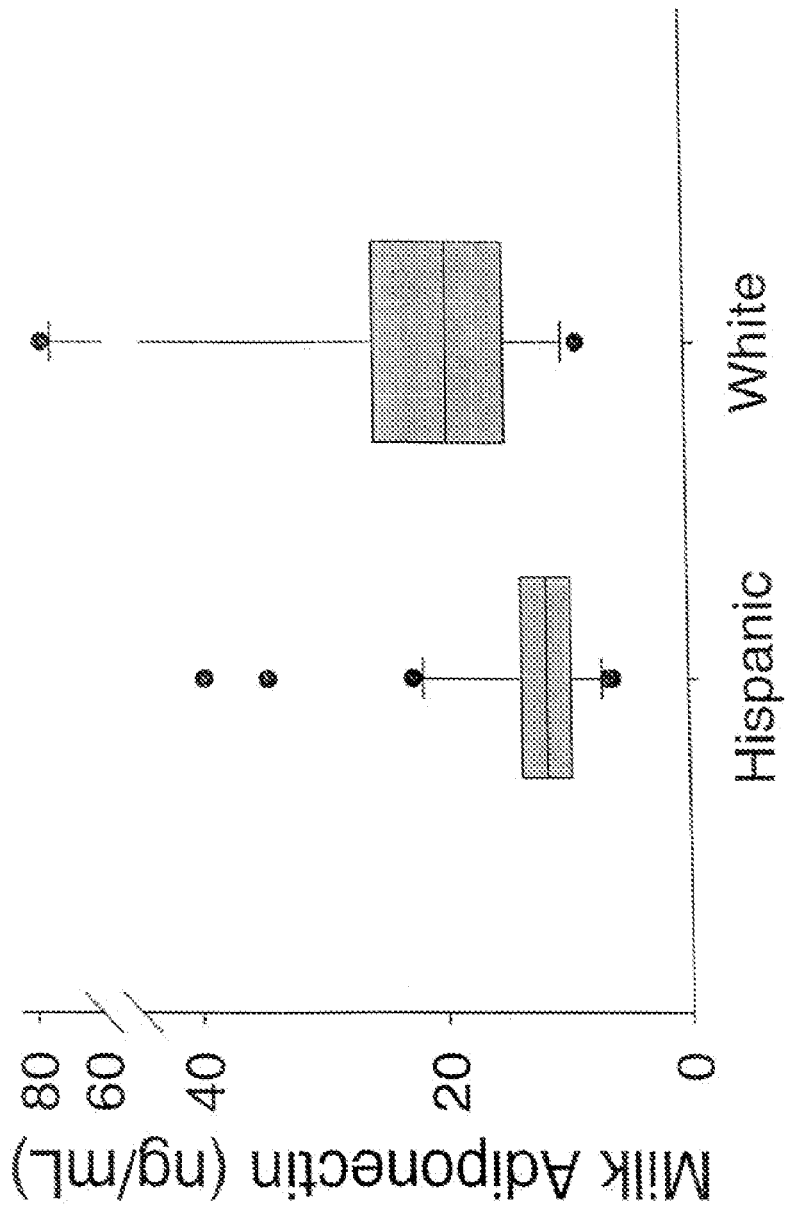
FIG. 3 is a graph depicting the relationship between milk adiponectin and ethnicity. Milk samples from approximately one-month lactation in 37 Mexican and 19 non-Hispanic white from the Cincinnati area women. Inter-quartile range defined by box; median represented by horizontal line. Whiskers represent 95th and 5th percentiles of distribution. Difference between medians: $p=0.003$ by Wilcoxon Signed Rank test.

In the RHMB-Ad hoc samples (n=30), month of lactation was negatively associated with ln(milk adiponectin), $\beta=-0.059\pm0.024$, p=0.02. These results were verified in RHMB-longitudinal samples, in which the month of lactation was also negatively associated with ln(milk adiponectin), $\beta=-0.059\pm0.007$, p<0.0001 (FIG. 2). Based on these results, milk adiponectin is predicted to be 6.9 ng/mL lower by 7 months' lactation compared with 1-week lactation.

Milk adiponectin concentrations decline throughout lactation. This is in agreement with previous studies documenting a decline of many milk proteins throughout lactation [15-17]. We also examined the effect of ethnicity on adiponectin concentrations. Hispanic mothers of Mexican descent had significantly lower concentrations of milk adiponectin than the non-Hispanic white donors at one-month lactation. These differences most likely have a physiological basis, as milk samples for non-Hispanic whites and Hispanics were collected using the same protocol, during the same period of lactation, and were assayed by the same individual, thereby minimizing sampling and assay error. Further, the ethnic difference in adiponectin concentration in milk parallels adiponectin concentrations in serum. Several studies have demonstrated that whites have higher serum adiponectin concentrations than Asians [54, 55], Amerindians [29], and African-Americans [56]. Although there has been no direct comparison serum concentration of adiponectin between Non-Hispanic whites and Hispanics, the Mexican population is considered to be primarily a combination of Amerindian and white populations [57]. Therefore, the finding of lower concentrations of adiponectin in milk in Mexicans is expected.

Human Milk Adiponectin is Associated with Post-Pregnancy Maternal Weight

Cross-sectionally in the RHMB-longitudinal cohort, post-pregnancy maternal BMI was significantly positively associated with ln(milk adiponectin) concentration at most time-points (Table 3). Even when statistical significance was not achieved, the magnitude of the relationship was relatively consistent from 1 to 7 months of lactation ($\beta$(range)=0.08 to 0.13, p(range)=0.01 to 0.16).

TABLE 3

Cross-sectional β Coefficients of Maternal BMI Regressed on ln(Milk Adiponectin) Concentration

| Month of Lactation | N | R-square (%) | β ± SE | p-value |
|---|---|---|---|---|
| 1 | 22 | 21.0 | 0.09 ± 0.04 | 0.03 |
| 2 | 22 | 16.1 | 0.08 ± 0.04 | 0.06 |
| 3 | 21 | 20.4 | 0.08 ± 0.04 | 0.04 |
| 4 | 20 | 26.2 | 0.10 ± 0.04 | 0.02 |
| 5 | 20 | 29.2 | 0.11 ± 0.04 | 0.01 |
| 6 | 15 | 29.2 | 0.13 ± 0.06 | 0.04 |
| 7 | 14 | 16.0 | 0.10 ± 0.07 | 0.16 |

Figure 4:
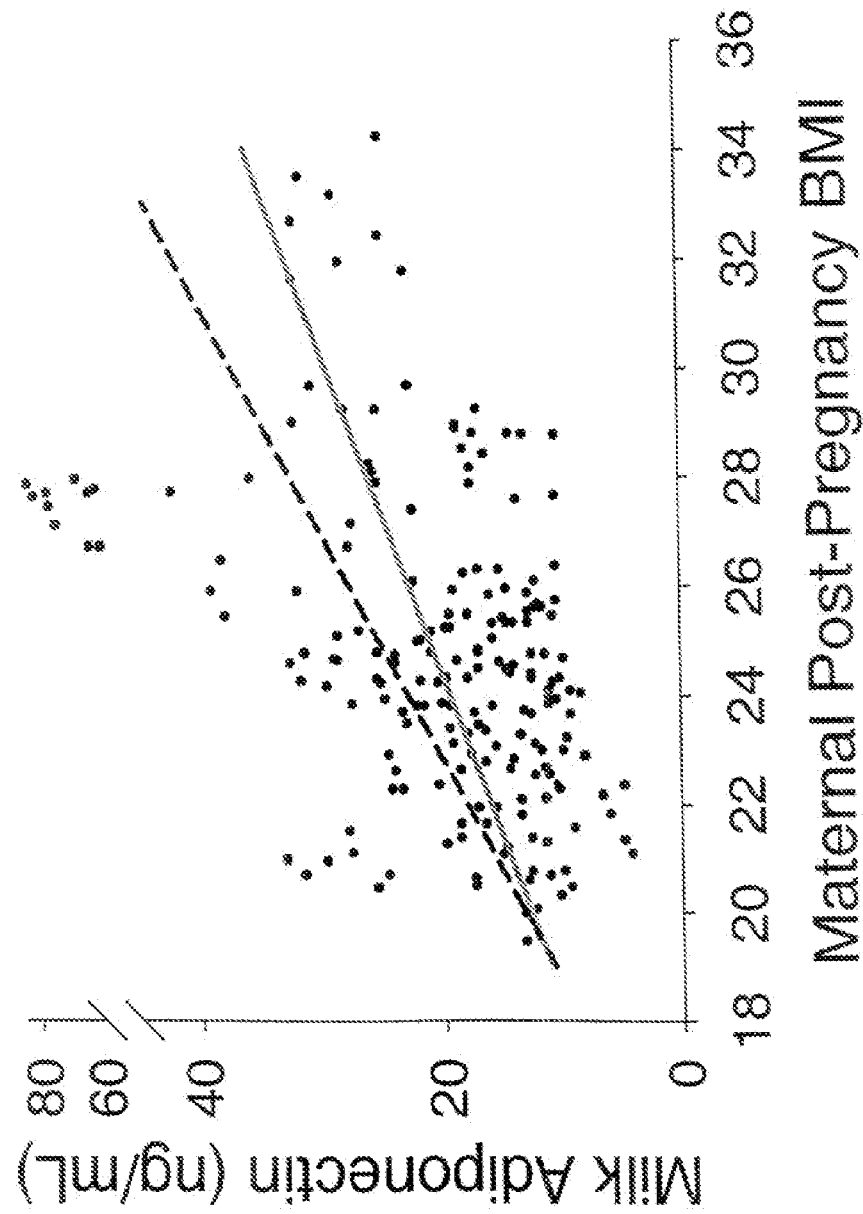
FIG. 4 is a graph depicting the relationship between milk adiponectin concentration by maternal BMI. Solid line is the predicted regression line determined from the repeated measures analysis of maternal BMI and ln(milk adiponectin), excluding two women (n=14 longitudinal samples) with milk adiponectin concentrations above 50 ng/mL ($\beta \pm SE$: $0.08 \pm 0.02$). Dashed line is the predicted regression line including these outliers ($\beta \pm SE$: $0.10 \pm 0.02$). A total of three data points from two individuals are not presented, with milk adiponectin concentrations between 45 and 60 ng/mL.

In longitudinal analyses (FIG. 4), maternal post-pregnancy BMI was significantly associated with ln(milk adiponectin) ($\beta=0.10\pm0.02$, p<0.0001). When excluding outlier milk adiponectin concentrations greater than 50 ng/mL (excluding 14 longitudinal values from 2 individuals), this relationship remained highly significant ($\beta=0.08\pm0.02$, p<0.0001).

In contrast to concentrations in serum, where adiposity is negatively correlated with adiponectin [58], a positive association was found between adiponectin concentrations in milk and maternal adiposity. One potential explanation for this finding is the relationship between adiponectin, prolactin and adiposity. Adiponectin is negatively regulated by prolactin [59, 60], a major determinant of mammary gland development in lactating women. Prolactin secretion is dampened in obesity [61, 62]. Thus, reduced negative regulation by prolactin in heavier mothers may positively impact concentrations of adiponectin produced locally in the breast tissue and its secretion into human milk.

Previous studies have demonstrated that milk components are not often degraded in the stomach, in part because the composition of human milk forms a protective environment for proteins [63] and in part because of the reduced acidity of the infant stomach [64] and limited gastric proteolysis [65]. Indeed, oral insulin is not degraded and thus can stimulate gut maturation [63, 66, 67]. As adiponectin has been demonstrated to increase insulin sensitivity [68, 69], it may also augment insulin's action in the infant gut. Adiponectin may also have direct effects on infant gut, as previous studies have documented that adiponectin receptor 1 is expressed in fetal small intestine [70].

Adiponectin in Human Milk is Associated with Infant Weight

Figure 5:
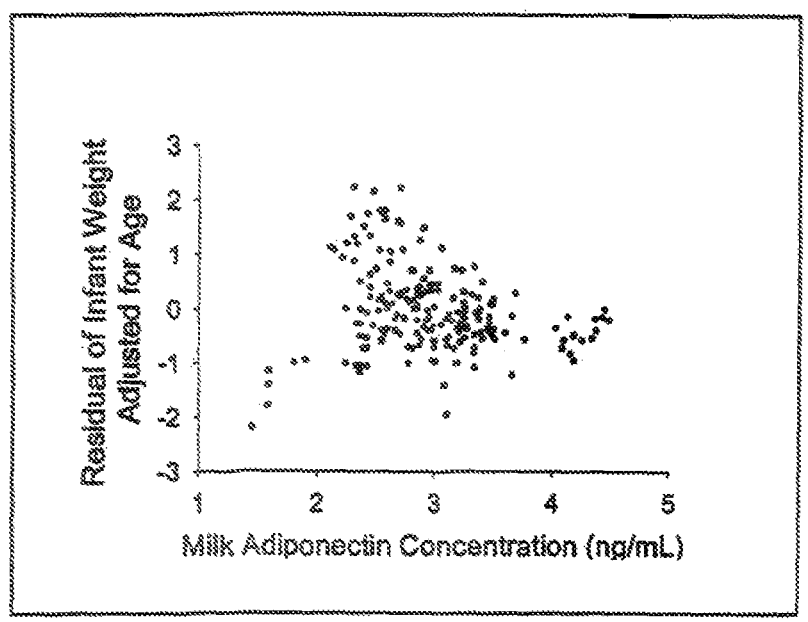
FIG. 5 is a graph depicting the relationship between milk adiponectin concentration and infant body weight.

Using the 22 sets of longitudinal samples from the CBC as described above, the longitudinal relationships between adiponectin in human milk and infant weight were explored. After accounting for the correlated structure of the data and repeated measures, adiponectin concentration in milk is negatively associated with weight gain in infants up to 28 weeks ($\beta\pm SE$: $-0.20\pm0.12$ kg, p=0.082), adjusting for infant age and age. While this relationship is not statistically significant, our small sample size was not powered to detect this effect. This relationship is displayed in FIG. 5 where the natural log of milk adiponectin is plotted against the residual of infant weight adjusted for age. To further examine the relationship between human milk adiponectin and infant growth, 36 samples collected at one month postpartum were randomly selected from a cohort of 306 Mexican mother-infant pairs. Despite differences in total milk adiponectin level between Mexican and U.S. mothers, correlations between the natural logarithm of milk adiponectin at one month and infant adiposity at one and four months postpartum is similar in magnitude in the Mexico and Cincinnati cohorts (Table 4).

TABLE 4

Correlations Between ln(milk Adiponectin) and Growth Status at One Month Post-partum

|  | Cincinnati | Mexico |
|---|---|---|
| N | 20 | 36 |
| Weight (kg) | −0.28 | −0.28* |
| Weight/Length (kg/m) | −0.28 | −0.28* |

(*= p < 0.10)

Figure 6:
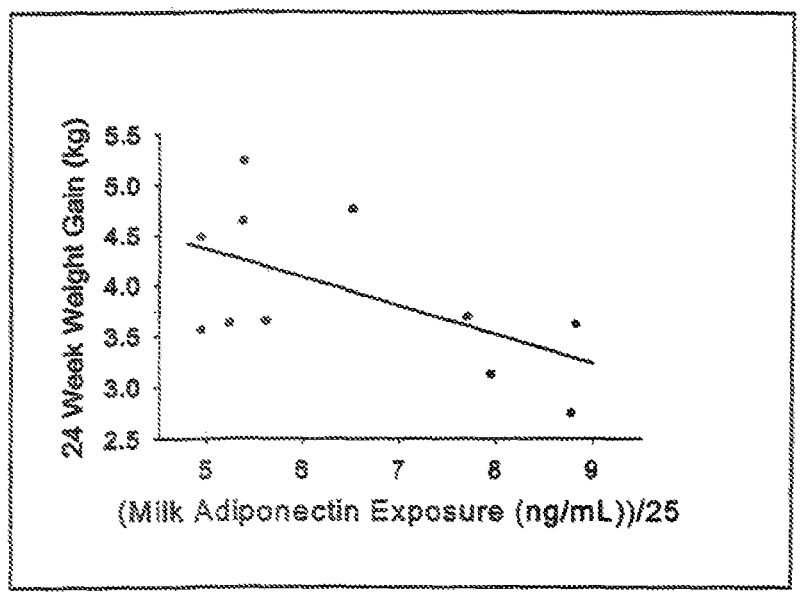
FIG. 6 is a graph depicting the relationship between adiponectin exposure and infant growth velocity.

Analysis of the milk adiponectin exposure metric in 11 mother-infant pairs with complete data revealed a cumulative exposure of infants to milk adiponectin by 24 weeks postpartum ranging from 123.2 to 220.5 ng/ml. This exposure metric, divided by 25 for more clinically meaningful interpretation, was negatively associated with infant growth velocity (weight gain) between birth and 24 weeks (growth velocity/24 weeks [kg]=5.76-0.28 [APN exposure], p=0.06, FIG. 6).

Thus, our data suggest that adiponectin in human milk is associated with lower weight among breastfed infants in the first six months of life, independent of age. These findings provide an intriguing potential explanation for why breastfed infants are typically leaner than formula fed infants.

Figure 7:
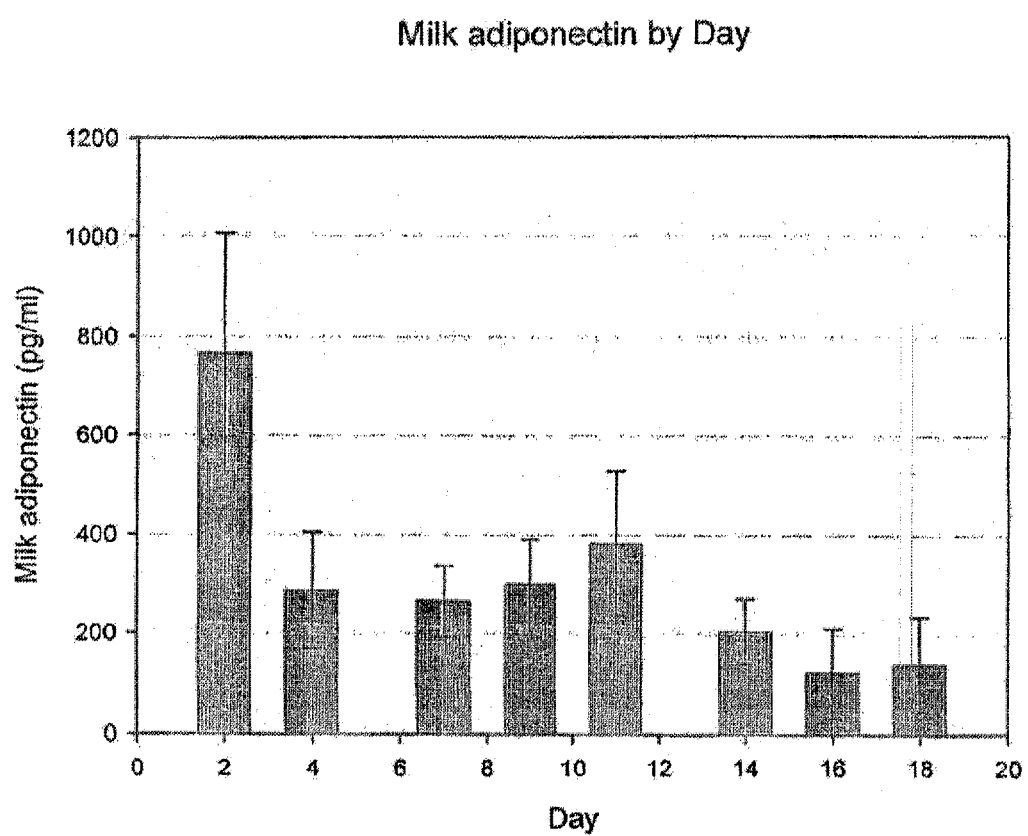
FIG. 7 is a graph depicting the level of adiponectin in mouse milk over the course of several days.
Figure 8:
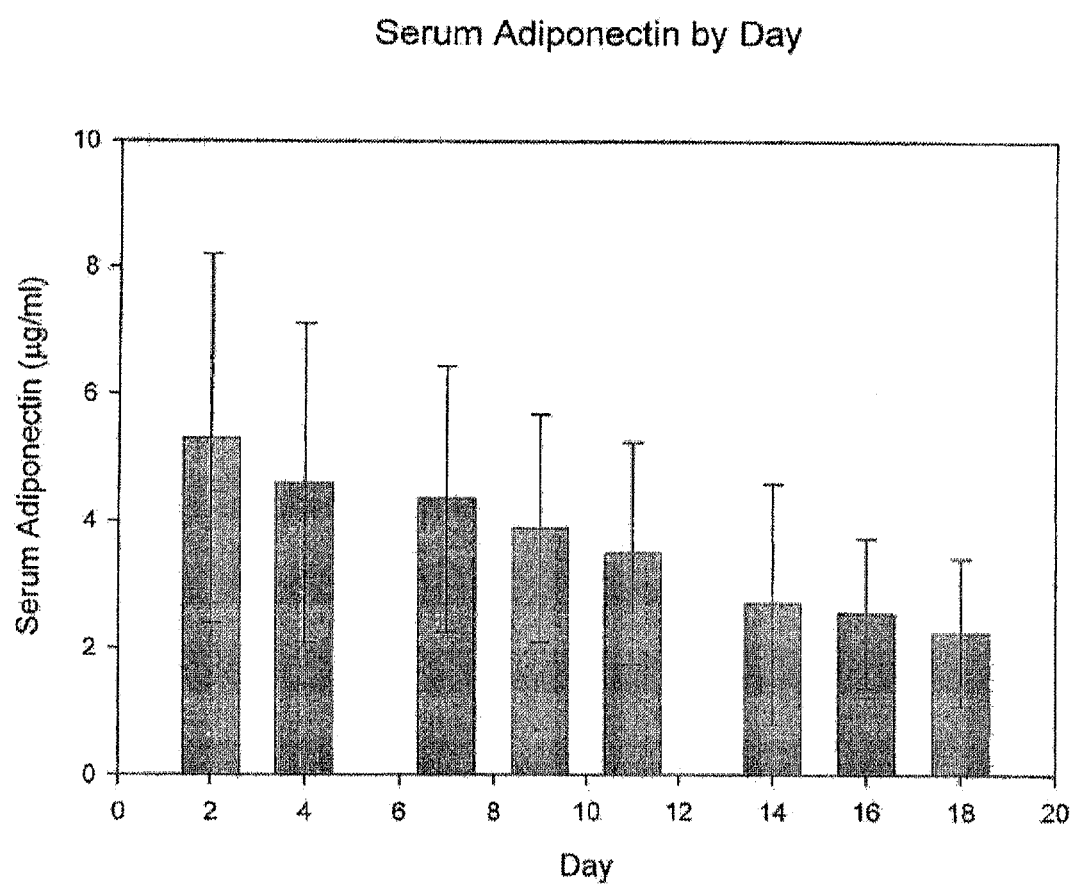
FIG. 8 is graph depicting the serum level of adiponectin in nursing mice over the course of several days.

Serum Adiponectin Levels in Nursing Mice Correlate with Adiponectin Levels in Mouse Milk The natural levels of adiponectin in mouse milk were measured over the course of lactation. It was found that adiponectin levels are highest early in lactation and lowest later in lactation (FIG. 7). If adiponectin in milk is absorbed into the serum, the levels in the serum of nursing pups should be influenced by differences in the level of adiponectin in consumed milk. Serum from the nursing pups was analyzed for adiponectin levels, and it was found that serum adiponectin is highest during the initial days of lactation and lowest late in lactation (FIG. 8). These data are consistent with milk adiponectin being a source of serum adiponectin in nursing mammals.

Orally Administered Adiponectin can be Absorbed into Serum

Figure 9:
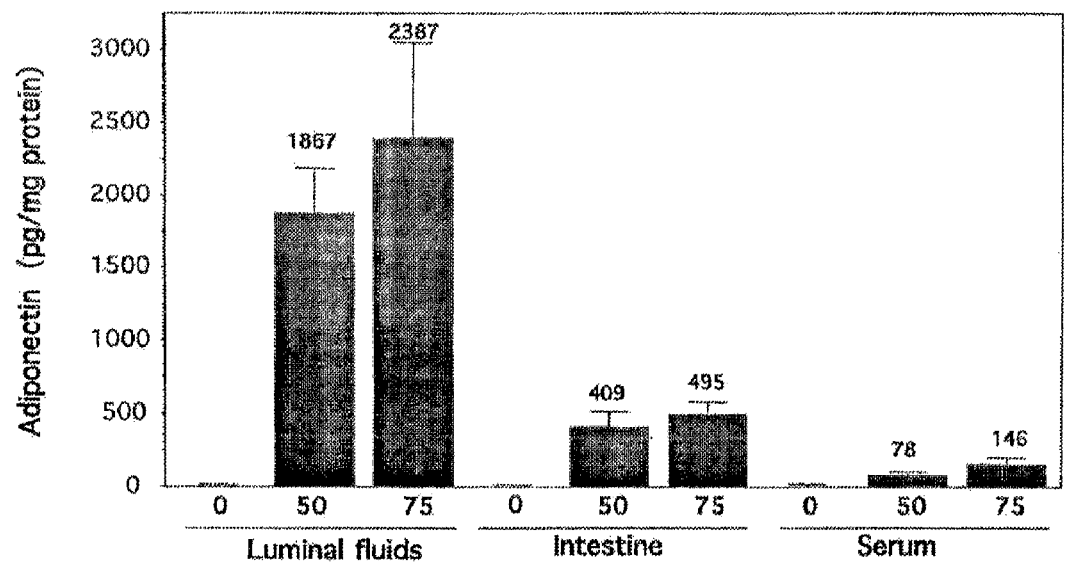
FIG. 9 is a graph depicting human adiponectin levels in the luminal fluids, intestine and serum of mice orally administered human adiponectin.

To measure the ability of adiponectin to cross the intestinal mucosa and be absorbed into the serum of young mammals, functional recombinant human adiponectin (expressed in mammalian cells) was orally administered to the stomach of mouse pups. Saline was administered as a control. Human adiponectin was measured in luminal fluids, the intestine and serum using an ELISA assay that is specific for human adiponectin. As shown in FIG. 9, the intestinal luminal fluid of mice that were orally administered human adiponectin contained levels of human adiponectin in proportion to the amount of human adiponectin administered. As shown in FIG. 9, the mice administered the highest amounts of human adiponectin had the highest levels of human adiponectin in the gut lumen, while those administered only saline had no human adiponectin in the gut lumen. Thus, oral administration successfully resulted in intact adiponectin in the gut. The human adiponectin was transported into the tissues of the gut, and again the mice administered the highest amounts of adiponectin had the highest levels in their intestinal tissues. Moreover, the human adiponectin administered into the gut was absorbed into the serum. As shown in FIG. 9, the mice administered the highest amount of human adiponectin exhibited the highest serum adiponectin levels. Thus, human adiponectin is able to be absorbed from the gut into the serum in young mammals, and the absorbed adiponectin could be responsible for the relationship between milk levels of adiponectin and physiologic consequences in the nursing infant.

Compositions Containing Adiponectin

Adiponectin can be administered in a composition that includes a pharmaceutically acceptable carrier, e.g., phosphate buffered saline solution, mixtures of ethanol in water, water and emulsions such as an oil/water or water/oil emulsion, as well as various wetting agents or excipients. Adiponectin can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose, diluents, lubricants, binders, disintegrating agents, and the like), etc. If desired, tablet dosages of the disclosed compositions may be coated by standard aqueous or nonaqueous techniques.

Adiponectin can be administered orally, e.g., as a tablet, pellet, gel, paste, syrup, bolus, electuary, slurry, capsule, powder, granules, as a solution or a suspension in an aqueous liquid or a non-aqueous liquid; as an oil-in-water liquid emulsion or a water-in-oil liquid emulsion, or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. Adiponectin can also be administered by rectal suppository, aerosol tube, naso-gastric tube, direct infusion into the GI tract or stomach or parenterally.

Pharmaceutical compositions containing adiponectin can also include therapeutic agents such as antiviral agents, antibiotics, probiotics, analgesics, and anti-inflammatory agents.

The proper dosage is determined by one of ordinary skill in the art and depends upon such factors as, for example, the patient's immune status, body weight and age. In some cases, the dosage will be at a concentration similar to that found for adiponectin present in human breast milk.

Adiponectin can also be added to other compositions. For example, it can be added to an infant formula or a nutritional composition or a milk fortifier (e.g., a human milk fortifier such as Enfamil™.

Adiponectin can be included in compositions that include macronutrients such as edible fats, carbohydrates and proteins. Edible fats include, for example, coconut oil, soy oil and monoglycerides and diglycerides. Carbohydrates include, for example, glucose, edible lactose and hydrolyzed cornstarch. Protein sources include, for example, protein source may be, for example, soy protein, whey, and skim milk.

Compositions, including nutritional compositions, containing the oligosaccharide agents can also include vitamins and minerals (e.g., calcium, phosphorus, potassium, sodium, chloride, magnesium, manganese, iron, copper, zinc, selenium, iodine, and Vitamins A, E, D, C, and B complex).

A number of embodiments of the invention have been described. Nevertheless, it will be understood that various modifications may be made without departing from the spirit and scope of the invention. Accordingly, other embodiments are within the scope of the claims.

REFERENCES

1. Gartner, L. M., et al., Breastfeeding and the use of human milk. Pediatrics, 2005. 115(2): p. 496-506.
2. Walker, W. A., The dynamic effects of breastfeeding on intestinal development and host defense. Adv Exp Med Biol, 2004. 554: p. 155-70.
3. Newburg, D. S., Innate immunity and human milk. J Nutr, 2005. 135(5): p. 1308-12.
4. Heird, W. C. and A. Lapillonne, The role of essential fatty acids in development. Annu Rev Nutr, 2005. 25: p. 549-71.
5. Jensen, C. L., et al., Effects of maternal docosahexaenoic acid intake on visual function and neurodevelopment in breastfed term infants. Am J Clin Nutr, 2005. 82(1): p. 125-32.
6. Khedr, E. M., et al., Neural maturation of breastfed and formula-fed infants. Acta Paediatr, 2004. 93(6): p. 734-8.
7. Scherer, P. E., et al., A novel serum protein similar to C1q, produced exclusively in adipocytes. J Biol Chem, 1995. 270(45): p. 26746-9.
8. Nakano, Y., et al., Isolation and characterization of GBP28, a novel gelatin-binding protein purified from human plasma. 1996. 120(4): p. 803-12.
9. Hu, E., P. Liang, and B. M. Spiegelman, AdipoQ is a novel adipose-specific gene dysregulated in obesity. The Journal of Biological Chemistry, 1996. 271(18): p. 10697-703.
10. Maeda, K., et al., cDNA cloning and expression of a novel adipose specific collagen-like factor, apM1 (AdiPose Most abundant Gene transcript 1). Biochem Biophys Res Commun, 1996. 221(2): p. 286-9.
11. Wulster-Radcliffe, M. C., et al., Adiponectin differentially regulates cytokines in porcine macrophages. Biochem Biophys Res Commun, 2004. 316(3): p. 924-9.
12. Kumada, M., et al., Association of hypoadiponectinemia with coronary artery disease in men. Arterioscler Thromb Vasc Biol, 2003. 23(1): p. 85-9.
13. Combs, T. P., et al., Endogenous glucose production is inhibited by the adipose-derived protein Acrp30., in The Journal of Clinical Investigation. 2001: United States. p. 1875-81.
14. Yamauchi, T., et al., Adiponectin stimulates glucose utilization and fatty-acid oxidation by activating AMP-activated protein kinase., in Nature Medicine. 2002: United States. p. 1288-95.
15. Tregoat, V., et al., Changes in the mannan binding lectin (MBL) concentration in human milk during lactation. J Clin Lab Anal, 2002. 16(6): p. 304-7.
16. Takahata, Y., et al., Detection of interferon-gamma-inducible chemokines in human milk. Acta Paediatr, 2003. 92(6): p. 659-65.
17. Itoh, H., et al., Hepatocyte growth factor in human breast milk acts as a trophic factor. Horm Metab Res, 2002. 34(1): p. 16-20.
18. Chowanadisai, W., et al., Detection of a single nucleotide polymorphism in the human alpha-lactalbumin gene: implications for human milk proteins. J Nutr Biochem, 2005. 16(5): p. 272-8.
19. Guerra, S., et al., The differential effect of genetic variation on soluble CD14 levels in human plasma and milk. Am J Reprod Immunol, 2004. 52(3): p. 204-11.
20. Uysal, F. K., et al., Breast milk leptin: its relationship to maternal and infant adiposity. Clin Nutr, 2002. 21(2): p. 157-60.
21. Hotta, K., et al., Plasma concentrations of a novel, adipose-specific protein, adiponectin, in type 2 diabetic patients., in Arteriosclerosis, Thrombosis, and Vascular Biology (Online). 2000: UNITED STATES. p. 1595-9.
22. Weyer, C., et al., Hypoadiponectinemia in obesity and Type 2 diabetes: Close association with insulin resistance and hyperinsulinemia, in Endocrinology and Metabolism. 2001. p. 1930-1935.
23. Cruz, M. L., et al., The metabolic syndrome in overweight Hispanic youth and the role of insulin sensitivity., in The Journal of Clinical Endocrinology and Metabolism. 2004: United States. p. 108-13.
24. Stefan, N., et al., Plasma adiponectin concentration is associated with skeletal muscle insulin receptor tyrosine phosphorylation, and low plasma concentration precedes a decrease in whole-body insulin sensitivity in humans., in Diabetes. 2002: United States. p. 1884-8.
25. Yamamoto, Y., et al., Adiponectin, an adipocyte-derived protein, predicts future insulin resistance: two-year follow-up study in Japanese population., in The Journal of Clinical Endocrinology and Metabolism. 2004: United States. p. 87-90.
26. Hanley, A. J., et al., Adiponectin in a native Canadian population experiencing rapid epidemiological transition., in Diabetes Care. 2003: United States. p. 3219-25.
27. Fumeron, F., et al., Adiponectin gene polymorphisms and adiponectin levels are independently associated with the development of hyperglycemia during a 3-year period: the epidemiologic data on the insulin resistance syndrome prospective study., in Diabetes. 2004: United States. p. 1150-7.
28. Spranger, J., et al., Adiponectin and protection against type 2 diabetes mellitus., in Lancet. 2003: England. p. 226-8.
29. Lindsay, R. S., et al., Adiponectin and development of type 2 diabetes in the Pima Indian population. Lancet, 2002. 360(9326): p. 57-8.
30. Daimon, M., et al., Decreased serum levels of adiponectin are a risk factor for the progression to type 2 diabetes in the Japanese Population: the Funagata study., in Diabetes Care. 2003: United States. p. 2015-20.
31. Snehalatha, C., et al., Plasma adiponectin is an independent predictor of type 2 diabetes in Asian indians., in Diabetes Care. 2003: United States. p. 3226-9.
32. Choi, K. M., et al., Serum adiponectin concentrations predict the developments of type 2 diabetes and the metabolic syndrome in elderly Koreans. Clin Endocrinol (Oxf), 2004. 61(1): p. 75-80.
33. Kubota, N., et al., Disruption of Adiponectin Causes Insulin Resistance and Neointimal Formation., in Journal of Biological Chemistry. 2002.
34. Berg, A. H., T. P. Combs, and P. E. Scherer, ACRP30/adiponectin: an adipokine regulating glucose and lipid metabolism. Trends Endocrinol Metab, 2002. 13(2): p. 84-9.
35. Fruebis, J., et al., Proteolytic cleavage product of 30-kDa adipocyte complement-related protein increases fatty acid oxidation in muscle and causes weight loss in mice, in PNAS. 2001. p. 2005-2010.

36. Ouchi, N., et al., Adiponectin, an adipocyte-derived plasma protein, inhibits endothelial NF-kappaB signaling through a cAMP-dependent pathway. Circulation, 2000. 102(11): p. 1296-301.
37. Yokota, T., et al., Adiponectin, a fat cell product, influences the earliest lymphocyte precursors in bone marrow cultures by activation of the cyclooxygenase-prostaglandin pathway in stromal cells. J Immunol, 2003. 171(10): p. 5091-9.
38. Chinetti, G., et al., Expression of adiponectin receptors in human macrophages and regulation by agonists of the nuclear receptors PPARalpha, PPARgamma, and LXR. Biochem Biophys Res Commun, 2004. 314(1): p. 151-8.
39. Kobayashi, H., et al., Selective suppression of endothelial cell apoptosis by the high molecular weight form of adiponectin. Circ Res, 2004. 94(4): p. e27-31.
40. Bobbert, T., et al., Changes of adiponectin oligomer composition by moderate weight reduction. Diabetes, 2005. 54(9): p. 2712-9.
41. Pajvani, U. B., et al., Structure-function studies of the adipocyte-secreted hormone Acrp30/adiponectin. Implications for metabolic regulation and bioactivity. J Biol Chem, 2003. 278(11): p. 9073-85.
42. Fisher, F. F., et al., Serum high molecular weight complex of adiponectin correlates better with glucose tolerance than total serum adiponectin in Indo-Asian males. Diabetologia, 2005. 48(6): p. 1084-7.
43. Pajvani, U. B., et al., Complex distribution, not absolute amount of adiponectin, correlates with thiazolidinedione-mediated improvement in insulin sensitivity. J Biol Chem, 2004. 279(13): p. 12152-62.
44. Tsao, T. S., et al., Oligomerization state-dependent activation of NF-kB signaling pathway by Acrp30. J Biol Chem, 2002.
45. Wang, Y., et al., Hydroxylation and glycosylation of the four conserved lysine residues in the collagenous domain of adiponectin. Potential role in the modulation of its insulin-sensitizing activity. J Biol Chem, 2002. 277(22): p. 19521-9.
46. Geraghty, S. R., et al., The development of a research human milk bank. J Hum Lact, 2005. 21(1): p. 59-66.
47. Houseknecht, K. L., et al., Leptin is present in human milk and is related to maternal plasma leptin concentration and adiposity. Biochem Biophys Res Commun, 1997. 240(3): p. 742-7.
48. Sivan, E., et al., Adiponectin in human cord blood: relation to fetal birth weight and gender. J Clin Endocrinol Metab, 2003. 88(12): p. 5656-60.
49. Lindsay, R. S., et al., Adiponectin is present in cord blood but is unrelated to birth weight. Diabetes Care, 2003. 26(8): p. 2244-9.
50. Yamamoto, K., et al., Production of adiponectin, an anti-inflammatory protein, in mesenteric adipose tissue in Crohn's disease. Gut, 2005. 54(6): p. 789-96.
51. Casabiell, X., et al., Presence of leptin in colostrum and/or breast milk from lactating mothers: a potential role in the regulation of neonatal food intake. J Clin Endocrinol Metab, 1997. 82(12): p. 4270-3.
52. Lyle, R. E., et al., Human milk contains detectable levels of immunoreactive leptin. Adv Exp Med Biol, 2001. 501: p. 87-92.
53. Smith-Kirwin, S. M., et al., Leptin expression in human mammary epithelial cells and breast milk. J Clin Endocrinol Metab, 1998. 83(5): p. 1810-3.
54. Abate, N., et al., Adipose tissue metabolites and insulin resistance in nondiabetic Asian Indian men. J Clin Endocrinol Metab, 2004. 89(6): p. 2750-5.
55. Raji, A., et al., Insulin resistance and vascular dysfunction in nondiabetic Asian Indians. J Clin Endocrinol Metab, 2004. 89(8): p. 3965-72.
56. Bacha, F., et al., Does adiponectin explain the lower insulin sensitivity and hyperinsulinemia of African-American children? Pediatr Diabetes, 2005. 6(2): p. 100-2.
57. Gorodezky, C., Genetic difference between Europeans and Indians: tissue and blood types. Allergy Proc, 1992. 13(5): p. 243-50.
58. Arita, Y., et al., Paradoxical decrease of an adipose-specific protein, adiponectin, in obesity. Biochem Biophys Res Commun, 1999. 257(1): p. 79-83.
59. Nilsson, L., et al., Prolactin and growth hormone regulate adiponectin secretion and receptor expression in adipose tissue, in Biochem Biophys Res Commun. 2005. p. 1120-6.
60. Combs, T. P., et al., Sexual differentiation, pregnancy, calorie restriction, and aging affect the adipocyte-specific secretory protein adiponectin., in Diabetes. 2003: United States. p. 268-76.
61. Kopelman, P. G., Physiopathology of prolactin secretion in obesity, in Int J Obes Relat Metab Disord. 2000. p. S104-8.
62. Kumar, A., et al., Reproductive functions in obese women, in Prog Food Nutr Sci. 1993. p. 89-98.
63. Lonnerdal, B., Nutritional and physiologic significance of human milk proteins. Am J Clin Nutr, 2003. 77(6): p. 1537S-1543S.
64. Henderson, T. R., et al., Gastric proteolysis in preterm infants fed mother's milk or formula. Adv Exp Med Biol, 2001. 501: p. 403-8.
65. Hamosh, M., Digestion in the newborn. Clin Perinatol, 1996. 23(2): p. 191-209.
66. Shehadeh, N., et al., Insulin in human milk: postpartum changes and effect of gestational age. Arch Dis Child Fetal Neonatal Ed, 2003. 88(3): p. F214-6.
67. Shulman, R. J., Oral insulin increases small intestinal mass and disaccharidase activity in the newborn miniature pig. Pediatr Res, 1990. 28(2): p. 171-5.
68. Yamauchi, T., et al., The fat-derived hormone adiponectin reverses insulin resistance associated with both lipoatrophy and obesity. Nat Med, 2001. 7(8): p. 941-6.
69. Berg, A. H., et al., The adipocyte-secreted protein Acrp30 enhances hepatic insulin action. Nat Med, 2001. 7(8): p. 947-53.
70. Zhou, Y., et al., Expression profiles of adiponectin receptors in mouse embryos. Gene Expr Patterns, 2005. 5(5): p. 711-5.

The invention claimed is:

1. A method for treating or reducing the risk of necrotizing enterocolitis comprising administering to an infant a composition containing a purified polypeptide that includes the amino acid sequence of an adiponectin or a biologically active fragment thereof, which is selected from the group consisting of 84-244, 85-244, 86-244, 87-244, 88-244, 89-244, 90-244, 91-244, 92-244, 93-244, 94-244, 95-244, 96-244, 97-244, 98-244, 99-244, 100-244, 101-244, 102-244, 103-244, 104-244, 105-244, 106-244, 107-244, 108-244, 109-244, 110-244, and 111-244 of SEQ ID NO: 1.

2. The method of claim 1, wherein the infant was born prematurely.

3. The method of claim 1, wherein the polypeptide is glycosylated and optionally hydroxylated.

4. The method of claim 1, wherein the polypeptide is an adiponectin or the biologically active fragment thereof.

5. The method of claim 4, wherein the composition further comprises lactose.

6. The method of claim 1, wherein the composition further comprises one or more oligosaccharides found in human milk, which are selected from the group consisting of facto-N-fucopentaose I [LNF-I], 2-fucosyllactose [2'-FL], lacto-N-difucohexaose I [LDFH-I], lactodifucotetraose [LDFT]), lacto-N-fuco-pentaose II [LNF-II], 3-fucosyllactose [3-FL], lacto-N-fucopentaose III [LNF-III], facto-N-tetraose [LNT], and lacto-N-neotetraose [LNneoT].

7. The method of claim 4, wherein the adiponectin is in the form found in human milk.

8. The method of claim 4, wherein the polypeptide is an adiponectin and the composition is administered at an amount to achieve a plasma concentration of the adiponectin between 1 μg/ml and 100 μg/ml.

9. The method of claim 4, wherein the adiponectin is in a complex containing at least two molecules of the adiponectin.

10. The method of claim 1, wherein the adiponectin or the biologically active fragment thereof is modified by at least one moiety selected from the group consisting of glucosylgalactosyl moiety, glucosylglucosyl moiety, galactosylglucosyl moiety, and galactosylgalactosyl moiety.

11. The method of claim 1, wherein the composition is administered orally.

* * * * *

UNITED STATES PATENT AND TRADEMARK OFFICE
CERTIFICATE OF CORRECTION

PATENT NO. : 8,314,061 B2
APPLICATION NO. : 12/160335
DATED : November 20, 2012
INVENTOR(S) : Ardythe L. Morrow et al.

Page 1 of 1

It is certified that error appears in the above-identified patent and that said Letters Patent is hereby corrected as shown below:

At column 1, after the "RELATED APPLICATIONS" paragraph, please insert:

--GOVERNMENT SUPPORT

This invention was made with government support under HD013021 awarded by the National Institutes of Health. The government has certain rights in this invention.--

Signed and Sealed this
Nineteenth Day of February, 2013

Teresa Stanek Rea
*Acting Director of the United States Patent and Trademark Office*

SEQUENCE LISTING

<160> NUMBER OF SEQ ID NOS: 3

<210> SEQ ID NO 1
<211> LENGTH: 244
<212> TYPE: PRT

<213> ORGANISM: Homo sapiens

<400> SEQUENCE: 1

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
                100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Asn His Tyr Asp
        130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
                180                 185                 190

Asn Val Asp Gln Ala Ser Gly Ser Val Leu Leu His Leu Glu Val Gly
            195                 200                 205

Asp Gln Val Trp Leu Gln Val Tyr Gly Glu Gly Glu Arg Asn Gly Leu
        210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 2
<211> LENGTH: 230
<212> TYPE: PRT
<213> ORGANISM: Homo sapiens

<400> SEQUENCE: 2

Gly His Asp Gln Glu Thr Thr Thr Gln Gly Pro Gly Val Leu Leu Pro
1               5                   10                  15

Leu Pro Lys Gly Ala Cys Thr Gly Trp Met Ala Gly Ile Pro Gly His
                20                  25                  30

Pro Gly His Asn Gly Ala Pro Gly Arg Asp Gly Arg Asp Gly Thr Pro
            35                  40                  45

Gly Glu Lys Gly Glu Lys Gly Asp Pro Gly Leu Ile Gly Pro Lys Gly
        50                  55                  60

Asp Ile Gly Glu Thr Gly Val Pro Gly Ala Glu Gly Pro Arg Gly Phe
65                  70                  75                  80

Pro Gly Ile Gln Gly Arg Lys Gly Glu Pro Gly Glu Gly Ala Tyr Val
                85                  90                  95

Tyr Arg Ser Ala Phe Ser Val Gly Leu Glu Thr Tyr Val Thr Ile Pro
            100                 105                 110

Asn Met Pro Ile Arg Phe Thr Lys Ile Phe Tyr Asn Gln Gln Asn His
            115                 120                 125

Tyr Asp Gly Ser Thr Gly Lys Phe His Cys Asn Ile Pro Gly Leu Tyr
    130                 135                 140

Tyr Phe Ala Tyr His Ile Thr Val Tyr Met Lys Asp Val Lys Val Ser
145                 150                 155                 160

Leu Phe Lys Lys Asp Lys Ala Met Leu Phe Thr Tyr Asp Gln Tyr Gln
                165                 170                 175

Glu Asn Asn Val Asp Gln Ala Ser Gly Ser Val Leu Leu His Leu Glu
            180                 185                 190

Val Gly Asp Gln Val Trp Leu Gln Val Tyr Gly Glu Gly Glu Arg Asn
        195                 200                 205

Gly Leu Tyr Ala Asp Asn Asp Asn Asp Ser Thr Phe Thr Gly Phe Leu
    210                 215                 220

Leu Tyr His Asp Thr Asn
225                 230

<210> SEQ ID NO 3
<211> LENGTH: 227
<212> TYPE: PRT
<213> ORGANISM: Homo sapiens

<400> SEQUENCE: 3

Gln Glu Thr Thr Thr Gln Gly Pro Gly Val Leu Leu Pro Leu Pro Lys
1               5                   10                  15

Gly Ala Cys Thr Gly Trp Met Ala Gly Ile Pro Gly His Pro Gly His
            20                  25                  30

Asn Gly Ala Pro Gly Arg Asp Gly Arg Asp Gly Thr Pro Gly Glu Lys
        35                  40                  45

Gly Glu Lys Gly Asp Pro Gly Leu Ile Gly Pro Lys Gly Asp Ile Gly
    50                  55                  60

Glu Thr Gly Val Pro Gly Ala Glu Gly Pro Arg Gly Phe Pro Gly Ile
65                  70                  75                  80

Gln Gly Arg Lys Gly Glu Pro Gly Glu Gly Ala Tyr Val Tyr Arg Ser
                85                  90                  95

Ala Phe Ser Val Gly Leu Glu Thr Tyr Val Thr Ile Pro Asn Met Pro
            100                 105                 110

Ile Arg Phe Thr Lys Ile Phe Tyr Asn Gln Gln Asn His Tyr Asp Gly
        115                 120                 125

Ser Thr Gly Lys Phe His Cys Asn Ile Pro Gly Leu Tyr Tyr Phe Ala
    130                 135                 140

Tyr His Ile Thr Val Tyr Met Lys Asp Val Lys Val Ser Leu Phe Lys
145                 150                 155                 160

Lys Asp Lys Ala Met Leu Phe Thr Tyr Asp Gln Tyr Gln Glu Asn Asn
                165                 170                 175

Val Asp Gln Ala Ser Gly Ser Val Leu Leu His Leu Glu Val Gly Asp
            180                 185                 190

Gln Val Trp Leu Gln Val Tyr Gly Glu Gly Glu Arg Asn Gly Leu Tyr
        195                 200                 205

Ala Asp Asn Asp Asn Asp Ser Thr Phe Thr Gly Phe Leu Leu Tyr His
    210                 215                 220

Asp Thr Asn
225